(12) United States Patent
Anglin et al.

(10) Patent No.: US 6,293,287 B1
(45) Date of Patent: *Sep. 25, 2001

(54) UV-CURED RESIN-COATED DENTAL FLOSS

(75) Inventors: David L. Anglin, Santa Clara; Casper W. Chiang, Danville, both of CA (US); Larry H. Luebbert, Iowa City, IA (US); Michael F. Roberts, Braintree, MA (US)

(73) Assignee: Gillette Canada Inc., Kirkland (CA)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/712,513

(22) Filed: Sep. 13, 1996

(51) Int. Cl.⁷ .................................................. A61C 15/00
(52) U.S. Cl. .................. 132/321; 427/175; 427/385.5; 427/386; 427/389.9; 427/558; 427/559
(58) Field of Search .................. 427/513, 558, 427/559, 175, 385.5, 386, 389.9; 132/321

(56) References Cited

U.S. PATENT DOCUMENTS

| | | | |
|---|---|---|---|
| 3,066,112 | 11/1962 | Bowen | 260/47 |
| 3,179,623 | 4/1965 | Bowen | 260/47 |

(List continued on next page.)

FOREIGN PATENT DOCUMENTS

| | | |
|---|---|---|
| 0 335 466 A2 | 6/1983 | (EP) . |
| 0 686 390 | 12/1995 | (EP) . |
| WO 93 02633 | 2/1993 | (WO) . |
| WO 9639117 | 12/1996 | (WO) . |

OTHER PUBLICATIONS

Derwent–Acc–No: 1982–35869E.*

Derwent–Acc–No: 1990–196898.*

Mark's Standard Handbook for Mechanical Engineer's, 9th Ed., pp. 5–13 (No date avail.).

Belsito (1989) "The Immunologic Basis of Patch Testing," J. Am. Acad. Dermatol. 21:822–9. (No month avail.).

*Primary Examiner*—Bernard Pianalto
(74) *Attorney, Agent, or Firm*—Fish & Richardson P.C.

(57) ABSTRACT

A dental floss having improved abrasion resistance composed of dental fibers coated with a UV-curable resin, and a method for producing a dental floss having improved abrasion resistance.

14 Claims, 2 Drawing Sheets

U.S. PATENT DOCUMENTS

| | | | |
|---|---|---|---|
| 3,256,266 | 6/1966 | Burt | 260/97.5 |
| 3,301,743 | 1/1967 | Fekete et al. | 161/194 |
| 3,616,149 | 10/1971 | Wincklhofer | 161/89 |
| 3,616,167 | 10/1971 | Gosden | 161/150 |
| 3,645,819 | 2/1972 | Fujii et al. | 156/148 |
| 3,679,541 | 7/1972 | Davis et al. | 161/175 |
| 3,699,979 | 10/1972 | Muhler et al. | 132/89 |
| 3,761,348 | 9/1973 | Chamberlin | 161/173 |
| 3,771,536 | 11/1973 | Dragan | 132/89 |
| 3,789,858 | 2/1974 | Pesce | 132/89 |
| 3,800,812 | 4/1974 | Jaffe | 132/89 |
| 3,837,351 | 9/1974 | Thornton | 132/89 |
| 3,838,702 | 10/1974 | Standish et al. | 132/89 |
| 3,896,824 | 7/1975 | Thornton | 132/89 |
| 3,897,795 | 8/1975 | Engel | 132/89 |
| 3,957,067 | 5/1976 | Ferraro et al. | 132/89 |
| 3,978,267 | 8/1976 | Selwood | 428/360 |
| 3,998,988 | 12/1976 | Shimomai et al. | 428/400 |
| 4,019,311 | 4/1977 | Schippers | 57/140 BY |
| 4,142,538 | 3/1979 | Thornton | 132/89 |
| 4,156,035 * | 5/1979 | Tsao et al. | |
| 4,230,766 * | 10/1980 | Gaussens et al. | 427/513 X |
| 4,259,457 * | 3/1981 | Login | 427/513 X |
| 4,263,370 * | 4/1981 | Login | 427/513 X |
| 4,275,117 | 6/1981 | Crandall | 428/373 |
| 4,380,435 | 4/1983 | Raeder et al. | 433/180 |
| 4,447,489 | 5/1984 | Linhart et al. | 428/225 |
| 4,477,525 * | 10/1984 | Login | 427/513 X |
| 4,514,438 * | 4/1985 | Gillberg-LaForce | 427/513 X |
| 4,583,564 | 4/1986 | Finkelstein et al. | 132/91 |
| 4,741,958 * | 5/1988 | Bishop | 427/513 X |
| 4,798,216 | 1/1989 | McCarty et al. | |
| 4,836,226 | 6/1989 | Wolak | 132/321 |
| 4,861,633 | 8/1989 | Abe | 428/36.3 |
| 4,974,615 | 12/1990 | Doundoulakis | 132/321 |
| 4,996,056 | 2/1991 | Blass | 424/443 |
| 4,998,978 | 3/1991 | Varum | 132/321 |
| 5,033,488 | 7/1991 | Curtis et al. | 132/321 |
| 5,039,549 * | 8/1991 | Nguyen et al. | 427/513 |
| 5,063,948 | 11/1991 | Lloyd | 132/321 |
| 5,076,300 | 12/1991 | Mayfield | 132/321 |
| 5,166,309 | 11/1992 | Maj et al. | 528/272 |
| 5,284,169 | 2/1994 | Gilligan et al. | 132/321 |
| 5,372,885 | 12/1994 | Tabor et al. | 428/373 |
| 5,393,516 | 2/1995 | Rheinberger et al. | 424/52 |
| 5,409,740 * | 4/1995 | Brann | 427/513 |
| 5,413,127 | 5/1995 | Hill | 132/321 |
| 5,433,226 | 7/1995 | Burch | 132/321 |
| 5,587,403 * | 12/1996 | Shustack | 427/513 X |
| 5,596,669 * | 1/1997 | Murphy et al. | 427/513 X |
| 5,842,489 * | 12/1998 | Suhonen et al. | |
| 5,878,758 * | 12/1998 | Bacino et al. | |

* cited by examiner

UV-CURED RESIN-COATED DENTAL FLOSS

BACKGROUND OF THE INVENTION

Tooth decay and dental disease can be caused by bacterial action resulting from the formation of plaque about the teeth and/or the entrapment of food particles in interstices between the teeth. Removal of plaque and entrapped food particles reduces the incidence of caries, gingivitis, and mouth odors as well as generally improving oral hygiene. Conventional brushing has been found to be inadequate for removing all entrapped food particles and plaque. To supplement brushing, dental flosses and tapes have been recommended.

Dental flosses including a thickened "brush" portion have been developed. These flosses may also include a thin "floss" portion and a threader. The brush portion, when drawn between tooth surfaces, provides good cleaning action which removes materials left by a standard thin floss used alone.

To form a brush floss, it is necessary to provide bulked filaments in a strand of floss, i.e., filaments which are separated and have a somewhat sinuous, random orientation.

Dental flosses, both in brush and thin floss form, often include additives such as flavors or colors. These flavors have been conventionally applied by coating the additive onto the surface of the floss.

Conventionally, polymers coating a filament are applied as solutions dissolved in a solvent. The production of polymer-covered filaments entails delay in the time required for the solvent to evaporate, generation of polluting solvent vapors, and the danger of residual unevaporated solvents. There is a need for improved filament coatings and for an improved method of producing a polymer-coated filament.

SUMMARY OF THE INVENTION

The present invention features a dental floss having improved abrasivity consisting of a dental filament coated with a UV-curable resin. Improved abrasivity is achieved by coating the fibers with a resin binder curable by exposure to ultraviolet (UV) radiation. Preferably, the resin is a composition comprising a clear oligomer resin and a UV-sensitive component. Preferably the oligomer resin is comprised of monomers having one or more cross-linkable functional groups such as acrylate or methacrylate. In specific embodiments, the monomers are epoxy acrylates, polyurethane acrylates, polyester acrylates, and acrylic acrylates. The UV-sensitive component is a photoinitiating compound which absorbs ultraviolet light and initiates polymerization of the monomers. In specific embodiments, the photoinitiating compound is benzoin, a benzoin alkyl ether, a benzyl ketal, an acetophenone derivative, a benzophenone, Michler's ketone, an α-acyloxime ester, a thioxanthone or a thioxanthone derivative, a quinone, anthraquinone or derivative, an organic peroxide, an organic sulfur compound, a metal compound or metal ion, an alkali dichromate, an organic phosphorus compound, a chlorosilane or an azo compound. In a preferred embodiment, the photoinitiator is benzophenone.

The UV-cured resin coated dental floss of the invention may further comprise additional components that provide desired floss properties and/or health treatment. In a preferred embodiment, the UV-cured resin includes a compound for control of the floss friction coefficient, e.g., abrasivity. In a specific embodiment, polytetrafluoroethylene (PTFE or Teflon®) powder is added to the UV resin formulation. In another embodiment, a compound is added to the UV-cured resin formulation for anti-caries tooth treatment. In a specifically preferred embodiment, the anti-caries treatment compound is sodium fluoride, stannous fluoride, or monosodium fluoride phosphate.

The UV-curable resin coated dental floss of the invention may have one or more distinct sections, including 1) a conventional floss section for cleaning the interproximal surfaces between the teeth, 2) a bulked brush section having improved abrasivity toward plaque and a larger dimension than the floss.

The coated dental filaments of the invention may be composed of mono filaments, e.g., filaments composed of one fiber, and multifilaments, e.g., strands having multiple fibers. Specific embodiments of the method of the invention include coating bulked or non-bulked filaments having a high or low elasticity, respectively, to produce dental floss having improved abrasivity.

The invention further features a method for producing a dental floss having improved abrasivity. An oligomer resin containing a photoinitiating system is coated onto a dental fiber and exposed to UV radiation such that the resin coat is cured to the desirable degree of hardness.

The method of the invention allows the degree of abrasivity of a floss to be controlled as desired.

One object of the invention is to provide a dental floss having improved abrasivity.

Another object of the invention is to provide an improved method of producing a coated dental floss having improved abrasivity.

One advantage of the invention is the production of a resin-coated dental floss without the use of solvents.

These and other objects, advantages and features of the present invention will become apparent to those persons skilled in the art upon reading the details of the compositions, composition components, methods and method steps of the invention as set forth below.

DETAILED DESCRIPTION

Before the present UV-cured resin coated dental floss and methods of production are described, it is to be understood that this invention is not limited to particular materials and methods described, as such materials and methods may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. The publications discussed above are provided solely for their disclosure prior to the filing date of the present application. Nothing herein is to be construed as an admission that the invention is not entitled to antedate such disclosure by virtue of prior invention.

Definitions

Figure 1:
FIG. 1 is a schematic representation of a dental floss having distinct floss, brush, and threader portions.

By the term "dental floss" is meant a filament or yarn suitable for use for removal of food particles in the interstices between teeth. A dental floss may be composed of a single filament (monofilament) yarn of a multifilament yarn, and may contain discrete sections of different thickness, e.g., a threader portion and a brush portion (FIG. 1).

By the term "UV-curable resin", "ultraviolet-curable resin", or "UV-cured resin", and the like, is meant a coating which achieves the desired degree of hardness upon exposure to ultraviolet radiation. This occurs due to the presence of a photoinitiating compound which absorbs UV light, generates a free radical, and causes cross-linking of functional groups on resin monomers.

By the term "cross-linkable functional group" is meant a chemical group, e.g., an acrylate or methacrylate, which is induced to react with another functional group upon activation by a free radical, resulting in cross-linking of the monomers containing the functional groups.

By the term "photoinitiator system" is meant a molecule which absorbs visible or ultraviolet light, forming an excited state which can then either fragment into free radical functional groups ("type I") capable of initiating polymerization of the monomers, or alter a second molecule by abstracting a hydrogen from the second molecule and converting the second molecule into a free radical capable of initiating polymerization ("type II" photoinitiator).

By the term "bulked" yarn is meant a multifilament strand composed of multiple individual filaments, where the individual filaments are in a random nonlinear conformation and remain entangled together. This results in an overall shortening of the overall length of a section of yarn relative to the length of the yarn when the filaments are placed under tension.

UV-Cured Resin Coated Dental Floss

The coating of solid material onto a dental material, such as dental floss, is generally achieved by dissolving the coating material in a solvent such as ethanol, acetone, ethyl acetate, triethylene glycol. Commonly used natural and synthetic resins are generally dissolved in a solvent, and the resin becomes hard after evaporation of the solvent. Examples of commonly used resins are shellac, benzoin resin, polyvinyl pyrrolidone, and colophony. U.S. Pat. No. 5,393,516 describes the coating of dental material with an antibacterial chlorhexidine adduct. The chlorhexidine adduct is formulated into a light-curing sealant applied with a paint-brush onto a molar fissure.

Dental filaments and flosses. Dental filaments for use in the flosses of the invention are preferably mono filaments or multifilaments. In one embodiment, the dental floss is manufactured as multicomponent coextruded filaments. By "multicomponent" is meant a filament having two or more components; by "coextruded" is meant that at least two of the components are present in the form of substantially separate phases having a distinct interface between them, rather than being intermixed. The filaments may be formed by processes referred to in the art as "coextruded", but may also encompass filaments having the structure described above which are manufactured by other processes known to the art.

The dental flosses having improved abrasivity include bulked and non-bulked fibers. A bulked nylon yarn alone is not adequate in stiffness to form an abrasive brush. If stretched or immersed in water its brush geometry will collapse. In order to provide brush abrasivity, a bulked yarn needs to have its geometry stabilized with a polymer overcoating. This coating acts to bind individual filaments of the bulked yarn together at contact points. The result of binding of filament to filament is a network structure similar to a fishing net but with three dimensions, which is flexible yet maintains its overall geometry when stretched or immersed. The abrasivity of such a bulked brush section is dependent on the properties of the polymer over-coating. If a brush section has a soft stretchy over-coating, the brush will be soft and stretchy; a hard brittle over-coating results in a brush with a hard brittle feel.

The properties of a dental floss when wet are important. If the bulked nylon brush polymer over-coating is water soluble, the brush structure is likely to collapse when wet. A highly hydrophilic coating will be overly softened when wet, resulting in decreased abrasivity of the floss and less effectiveness for plaque removal.

Ultraviolet radiation-curable resins. Any natural or synthetic resin can be used for coating the dental floss. The resin is composed of a mixture of crosslinkable resin or resins and a UV-sensitive component which initiates polymerization upon exposure to UV radiation. Preferably, the resin is a clear copolymer resin of a relatively high molecular weight, such as a polyurethane with molecular weight 1000.

A variety of resinous compositions are known in the art to be susceptible to crosslinking by means of exposure to free radicals derived from excitation of added photoinitiators by (UV) radiation. Certain acrylate, methacrylate, and bismaleate vinyl ether blends are susceptible; see, for example, U.S. Pat. Nos. 3,066,112, 3,179,623, 3,256,266, and 3,301,743. Resinous composition such as urethane acrylates can be combined with radiation sensitive initiators such as benzophenone, and are cured upon exposure to UV radiation. In thin films, the cure can be accomplished in less than 1 second. Methods of photocuring a UV-sensitive resin are known in the art. See, for example, U.S. Pat. No. 4,380,435.

Traditional UV-curable resins have molecular weights from 150 to 550. Generally, larger molecules pose a decreased toxicity risk than smaller molecules. For example, UV-curable monomer trimethylolpropane triacrylate (TMPTA) has a molecular weight of 296 and a toxicity (Drais) value of 5. When the molecular weight of TMPTA is increased to 912 by ethoxylation, the toxicity value drops to 0. Accordingly, the preferred oligomer monomer used in the present invention, such as polyurethane, has a high molecular weight, e.g., 1000.

The UV-curable resin of the present invention is composed of a monofunctional or multifunctional monomer molecule and a photoinitiating compound. Monomers typically used for UV curing have an acrylate or methacrylate functional groups. The number of acrylate, methacrylate, bismaleates and vinyl ether groups per monomer molecule is typically two, e.g., diacrylates or dimethacrylates, but monomers may be monofunctional or multifunctional.

Photoinitiators and photosensitizers absorb ultraviolet light to form free radical groups which can initiate polymerization. A critical element in the selection of the appropriate photoinitiating compound is that it absorb light at a wavelength at which the remaining resin components do not absorb. Further, the appropriate photoinitiator must be soluble in the selected resin monomer. Additionally, the photoinitiator must have a high activity so that it initiates polymerization at very low concentrations, and must be nontoxic to humans in the final polymer. Suitable photoinitiators include benzoins, benzoin alkyl ethers, benzyl ketals, acetophenone derivatives, benzophenones, Michler's ketone, α-acyloxime esters, thioxanthones or thioxanthone derivatives, quinones, anthraquinones or derivatives, organic peroxides, organic sulfur compounds, metal compounds or metal ions, alkali dichromates, organic phosphorus compounds, chlorosilanes and azo compounds.

Polymerization of the resin on the floss/filament material is accomplished by exposure of the UV-sensitive photoinitiator and free radical curable resin to UV radiation. Preferably, the source of UV radiation is a medium pressure mercury arc lamp. For example, resin-covered floss can be exposed to UV radiation from a commercial 85 watt Mercury vapor lamp for a time sufficient to cure the resin. Other sources of UV radiation known in the art may be used in the method of the invention such that the resin exhibits a desired hardness value, as determined by methods known in the art, including Barcoll or Vickers hardness scores (Mark's Standard Handbook for Mechanical Engineers, 9th Ed., pp. 5–13).

Degree of cure is determined by measuring the solubility of the cured UV polymer in an appropriate organic solvent. Uncured monomers are completely soluble in organic solvents and will extract out of a partially cured UV resin into an appropriate solvent. Extraction amount decreases as degree of cure increases. A fully cured, cross-linked polymer will be insoluble in solvents. Additives which do not crosslink with the UV resins such as type II photoinitiators or their reaction products will be extractable after the UV resin polymerizes.

The degree of cure of the UV-cured floss of the invention is determined by refluxing the floss in a suitable solvent. For example, in one method of determining degree of cure, refluxing floss that has been coated with a UV-curable coating in placed in 50:50 water/ethanol for 24 hours; the solvent is decanted and evaporated, and the residue weighed. The determination of the extractable portion of the coating provides a measure of the degree of cure.

This degree of cure extraction test can be used to optimize the UV exposure required to cure a UV coating for specific coating formulations. A UV curable mixture can be coated onto the floss, passed through a 300 watt per inch medium pressure mercury arc UV lamp at a variety of speeds, and the percent extractable content after refluxing for 24 hours in a 50:50 water/ethanol solution determined.

Production of a UV-resin coated dental floss for use in the oral cavity of a human requires the careful selection of materials which will produce a floss with the desired mechanical and safety characteristics. The present invention provides a series of test protocols and test results that must be achieved in order to achieve the UV-resin coated dental floss of the invention. Specifically, final UV-cured resins and photoinitiating compounds must be nontoxic to humans and nonsensitizing in the oral cavity.

In the method of the invention, one or more specific compounds can be added to the UV-curable resin coating for controlling the floss friction coefficient. In one embodiment, the compound added for controlling the floss friction coefficient is polytetrafluoroethylene (PTFE). A preferred floss friction coefficient is between 0.08 and 0.25. PTFE has a coefficient of friction value of 0.04. The addition of PTFE to the UV resin composition results in a lowering of the coefficient of friction value of the floss.

The Examples below describe the test protocols used to evaluate the acceptability each component of the UV-curable resin composition in terms of toxicity (Example 1) and mechanical properties such as abrasiveness, brittleness, and flexibility (Example 2). Example 3 describes the test protocols used to determine important processibility characteristics, for example, ease of handling (viscosity and sensitivity to UV light (λ)).

Example 4 evaluates three UV-cured resin formulations for the threader portion of a dental floss in terms of their mechanical and toxic properties. Example 5 provides detailed toxicity results for a UV-cured resin formulated for application to the brush portion of a dental floss. Example 6 evaluates a UV-cured coating formulation in terms of percent extractables and toxicity.

EXAMPLES

The following examples are put forth so as to provide those of ordinary skill in the art with a complete disclosure and description of how to make and use various UV-curable resin compositions and perform the various methods of the present invention and are not intended to limit the scope of what the inventors regard as their invention. Unless indicated otherwise, parts are parts by weight, temperature is in degrees centigrade, and pressure is at or near atmospheric pressure. Efforts have been made to ensure accuracy with respect to numbers used, (e.g., molecular weights, amounts, particular components, etc.) but some deviations should be accounted for.

Example 1

Acceptability Test Protocols

Toxicity Test. Cytotoxicity is evaluated by using the USP Elution Test Method (MG057), which measures the biological reactivity of polymeric materials. Briefly, monolayers of L-929 mouse fibroblast cells were grown to confluency in duplicate flasks and exposed to an extract of the test article. The extract was prepared according to USP guidelines by placing the test article in 13 ml of MEM and extracting for 24 hours at 37° C. The current NAmSA positive control was used as a positive control and a USP negative bioreaction control was used as a negative control. The cells were examined for evidence of cytotoxic effect after exposure to the extracts for 48 hours at 37° C. Reactivity and grade were recorded according to Table 1. The NAmSA positive control was scored at 24 hours. The test article meets the requirements of USP if the biological response is less than or equal to grade 2 (Mild).

TABLE 1

| GRADE | REACTIVITY | OBSERVATIONS |
| --- | --- | --- |
| 0 | None | Discrete intracytogranules; no cell lysis |
| 1 | Slight | Not more than 20% of cells are round, loosely attached and without intracytoplasmic granules; some lysed cells are present |
| 2 | Mild | Not more than 50% of the cells are round and devoid of intracytoplasmic granules; extensive cell lysis and empty areas between cells |
| 3 | Moderate | Not more than 70% of the cell monolayer contain rounded and/or lysed cells |
| 4 | Severe | Nearly complete destruction of the cell monolayer |

Sensitization Test. Sensitization was measured with the Repeated Insulin Patch Test (RIPT) (Belsity (1989) J. Am. Acad. Dermatol. 21:822–829). 40 grams of floss or threader were incubated at 37° C. in 200 ml of 0.9% saline for 24 h. The saline was then sterilized by filtration through a 0.2 micron filter. In the "induction phase" of the test, approximately 0.2 ml of the test solution was applied as a patch to the back of the hand adjacent to the spinal mid-line of 50 male or female adult human volunteer subjects. The subjects were instructed to remove the patch 24 h after application. The procedure was repeated 3 times per week (Monday, Wednesday, Friday) for 3 weeks. 24 h rest periods followed the Tuesday and Thursday patch removals; a 48 h rest period followed the Saturday patch removal. The application site was scored just prior to each test application according to the following 6 point scale: 0, no evidence of any effect; +, barely perceptible (minimal, faint, uniform, or spotty erythema); 1, mild (pink, uniform erythema covering most of the contact site); 2, moderate (pink-red erythema uniform in the entire contact site); 3, marked (bright red erythema with/without petechiae or papules); and 4, severe (deep red erythema with/without vesiculation or weeping).

In the challenge phase of the sensitization test, a challenge patch with the same amount of test extract previously applied was applied to a previously unpatched test site approximately 2 weeks after the induction phase was complete. The site was scored 24 and 72 h after application.

Flexibility and brittleness. Flexibility and brittleness are measured using an Instron stress strain tester on cast films of polymer (ASTM D638).

Viscosity. Viscosity is determined with a rheometer having cone and plate geometry, constant stress mode (TA Associates).

Sensitivity to UV light ($\lambda$). The UV-visible light absorption spectra of resin and resin+photoinitiator is compared. A basic requirement for suitable resin and photoinitiator systems is that the photoinitiator absorbs UV radiation at a $\lambda$ different from that of the resin.

Example 2

UV-Sensitive Resins on Threader Portion of Floss

The following formulas were evaluated by coating onto 640 denier yarn at 15 feet per minute and UV curing with a 300 watt per inch medium pressure mercury vapor light:

1. Cationic System

| Union Carbide Cyracure 6110 | 84% |
| Union Carbide PEG 300 | 11% |
| Union Carbide 6990 | 5% |
| FD&C Lake Pigment | 0.15% |

Test results: The resin provided adequate stiffness, but had an irregular surface. The resin failed the cytotoxicity test (4).

2. Bisphenol Epoxy Diacrylate System

| Radcure Ebecryl 3200 | 71% |
| Radcure Ebecryl 600 | 22% |
| Radcure Ebecryl BPO | 7% |
| FD&C Lake Pigment | 0.15% |

Test results: The resin provided adequate stiffness and a smooth surface. The resin failed the cytotoxicity test (4).

3. Polyurethane Diacrylate and Hexaacrylate Blend

| Radcure Ebecryl 8402 | 46.5% |
| Radcure Ebecryl 220 | 46.5% |
| Radcure Ebecryl BPO | 7% |
| FD&C Lake Pigment | 0.15% |

Test results: The resin provided adequate stiffness and a smooth surface. The resin passed the cytotoxicity test (0).

Example 3

UV-Sensitive Resins on Brush Portion of Floss

A resin having a softer finish is preferred for coating onto the brush portion of dental floss. The following formula was evaluated by coating onto 640 denier nylon yarn at 15 feet per minute and UV curing with a 300 watt per inch medium pressure mercury vapor light:

Brush Formula

| Radcure Ebecryl 8402 | 93% |
| Radcure Ebecryl BPO | 7% |

Toxicity Results: The Radcure 8402 formulation had a cytotoxicity score of "1" (Table 2).

TABLE 2

| | A | B | Negative Control A | Negative Control B |
|---|---|---|---|---|
| Confluent Monolayer | — | — | + | + |
| % Cells without Intracellular Granulation | 10 | 10 | 0 | 0 |
| % Rounding | 10 | 10 | 0 | 0 |
| % Lysis | 10 | 10 | 0 | 0 |
| Grade | 1 | 1 | 0 | 0 |
| Reactivity | Slight | Slight | None | None |

Example 4

Production of UV-cured Resin Coated Dental Floss Threader

Figure 2:
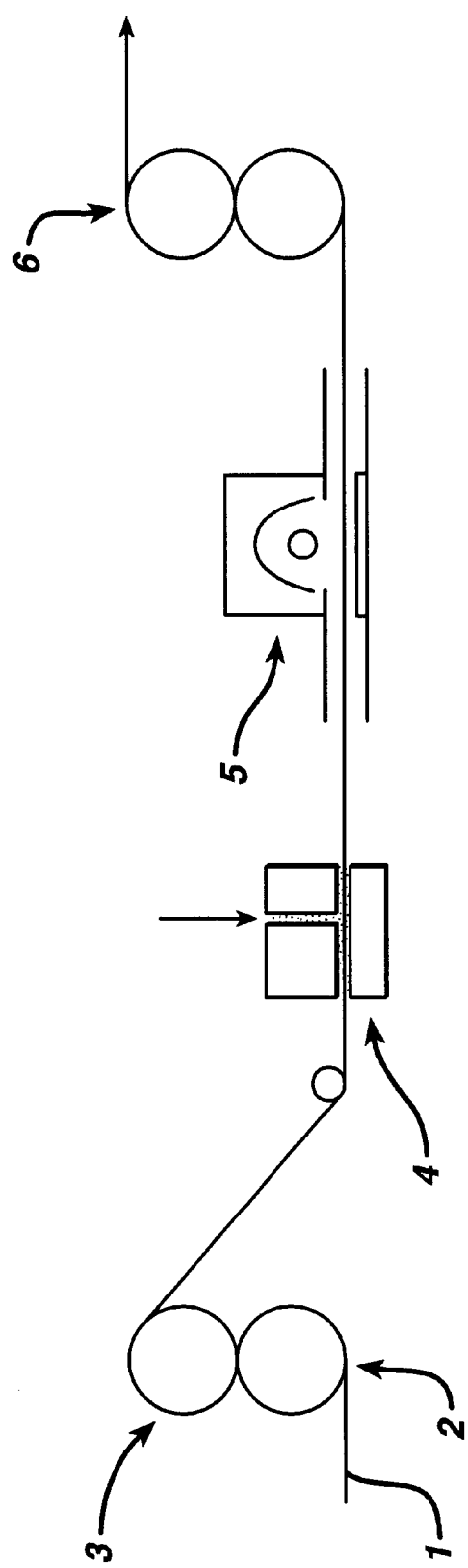
FIG. 2 illustrates a method of coating a yarn with the UV-cured resins of the invention. Yarn (1) is coated at a station consisting of a yarn unwind station (2), a tensioning device (3), a coating die (4), a medium pressure mercury arc lamp (5), and a speed controlled winding station (6).

Coating of floss with UV resins was accomplished on a coating line consisting of a yarn unwind station, a tensioning device, a coating die (FIG. 2), a medium pressure mercury arc lamp, and a speed controlled winding station. The UV curable resin was supplied to the extrusion die through a side injection port where it is delivered to the yarn at a controlled rate. The exit orifice of the extrusion die was sufficiently narrow to spread the UV resin uniformly on the yarn.

The coating composition Radcure 8402:220:BPO (46.5:46.5:5:7) was coated and cured as described above at a variety of speeds, and percent extractables determined. The following results were obtained with the use of a Fusion Systems Model F300 medium pressure mercury arc UV lamp.

The stiffness of this composition was compared with that of the conventional solvent-based polyurethane threader. As measured by Gurley stiffness, the conventional threader had a stiffness of 2.8 with a 38% coating (% of yarn substrate), while the UV formulation had a stiffness of 3.3 with a lower coating weight of 33%.

TABLE 3

| Speed (ft/min) | UV Exposure Time (sec) | % Extractable | Cytotoxicity |
|---|---|---|---|
| 22.5 | 0.89 | 1.1 | 0 |
| 26 | 0.77 | 1.0 | 0 |
| 30 | 0.67 | 1.7 | 4 |

Example 5
Fluoride-Containing UV-Sensitive Resins

Sodium fluoride (2.2%, 4.4%, and 6.6%) was added to a 95:5 ratio of Radcure 8402 and BPO. After coating and UV curing onto nylon yarn as described in Example 3 above, the release of fluoride was measured. Fluoride release was determined by stirring a 10 meter length of floss in TISAB II water and measuring the fluoride concentration with an Orion 96-09BN fluoride specific electrode. The results are shown in Table 4:

TABLE 4

| Radcure 8402:BPO (% sodium fluoride) | Sodium Fluoride Release (mg/0.5 m floss) |
|---|---|
| 2.2 | 0.05 |
| 4.4 | 0.15 |
| 6.6 | 0.20 |
| Commercial Floss | 0.16 |

The method used to add sodium fluoride to commercially available dental floss was adding sodium fluoride to a wax, and coating the wax onto nylon yarn. The addition of sodium fluoride to a commercial floss was found to weaken the wax coating, resulting in a dental floss more prone to fray between teeth. In contrast, the UV-cured floss containing sodium fluoride was not prone to fraying.

Example 6
UV-Cured Dental Floss with Altered Geometry

A UV-cured dental floss with flattened geometry was produced by first coating nylon yarn as with the composition of Example 3 above, and UV-curing the floss while it was in contact with the surface of a drum. This allowed the coated uncured floss to flatten against the drum surface and to be fixed in that geometry by exposure to UV light. A flattened floss was found to be easier to insert between teeth relative to floss having a round geometry.

The instant invention is shown and described herein in what is considered to be the most practical, and preferred embodiments. It is recognized, however, that departures may be made therefrom which are within the scope of the invention, and that modifications will occur to one skilled in the art upon reading this disclosure.

What is claimed is:

1. A method of producing a dental floss coated with a UV-cured resin, comprising the steps of:
   a) preparing a coating composition containing a monomer having one or more cross-linkable functional groups, wherein said monomer is selected from the group consisting of epoxy acrylate, polyurethane acrylate, polyester acrylate, acrylic acrylate, epoxy methacrylate, polyurethane methacrylate, polyester methacrylate and acrylic methacrylate, and (b) a photoinitiating compound;
   b) coating a dental filament with the coating composition of step a); and
   c) exposing the coated filament from step b) to UV radiation to cause the coating composition to be cured to a desired degree of hardness;
   wherein, after step c), said coating composition is safe for use in the mouth.

2. A dental floss comprising:
   a filament coated with a cross-linked resin composition, the resin composition comprising, prior to cross-linking:
   a monomer that polymerizes and cross-links when exposed to ultraviolet light, and
   a photoinitiating compound.

3. The dental floss of claim 2, wherein said filament is comprised of a threader portion and a brush portion.

4. The dental floss of claim 2, wherein said monomer is selected from the group consisting of epoxy acrylate, polyurethane acrylate, polyester acrylate, acrylic acrylate, epoxy methacrylate, polyurethane methacrylate, polyester methacrylate, and acrylic methacrylate.

5. The dental floss of claim 4, wherein said photoinitiating compound is selected from a benzoin, a benzoin alkyl ether, a benzyl ketal, an acetophenone derivative, a benzophenone, Michler's ketone, an α-acyloxime ester, a thioxanthone or a thioxanthone derivative, a quinone, anthraquinone or derivative, an organic peroxide, an organic sulfur compound, a metal compound or metal ion, an alkali dichromate, an organic phosphorus compound, a chlorosilane and an azo compound.

6. The dental floss of claim 5, wherein said photoinitiating compound comprises benzophenone.

7. The dental floss of claim 4, wherein said resin further comprises an anti-caries compound.

8. The dental floss of claim 7, wherein said anti-caries compound is sodium fluoride, stannous fluoride, or monosodium fluoride phosphate.

9. The dental floss of claim 4, said resin comprises a compound for controlling the floss friction coefficient.

10. The dental floss of claim 9, wherein said compound for controlling the floss friction coefficient is polytetrafluoroethylene (PTFE).

11. The dental floss of claim 2, wherein said filament is a monofilament or a multifilament.

12. The dental floss of claim 11, wherein said filament is a bulked multifilament.

13. The dental floss of claim 11, wherein said filament is a nonbulked multifilament.

14. An article comprising
   a filament coated with a resin comprising a monomer and a photoinitiating compound, wherein the monomer polymerizes and cross-links when exposed to ultraviolet light, providing a dental floss.

* * * * *

UNITED STATES PATENT AND TRADEMARK OFFICE
CERTIFICATE OF CORRECTION

PATENT NO.    : 6,293,287 B1
DATED         : September 25, 2001
INVENTOR(S)   : Michael Roberts et al.

It is certified that error appears in the above-identified patent and that said Letters Patent is hereby corrected as shown below:

<u>Column 10,</u>
Line 43, after "resin", insert -- further --.

Signed and Sealed this

Twentieth Day of May, 2003

JAMES E. ROGAN
*Director of the United States Patent and Trademark Office*